(12) United States Patent
Karp et al.

(10) Patent No.: US 11,287,408 B2
(45) Date of Patent: Mar. 29, 2022

(54) GAS SENSOR INCLUDING OPTIC FIBER CONNECTOR

(71) Applicants: Jason Harris Karp, Niskayuna, NY (US); William Albert Challener, Glenville, NY (US)

(72) Inventors: Jason Harris Karp, Niskayuna, NY (US); William Albert Challener, Glenville, NY (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 205 days.

(21) Appl. No.: 16/398,665

(22) Filed: Apr. 30, 2019

(65) Prior Publication Data

US 2019/0339240 A1 Nov. 7, 2019

Related U.S. Application Data

(60) Provisional application No. 62/665,218, filed on May 1, 2018.

(51) Int. Cl.
| | |
|---|---|
| *G01N 33/00* | (2006.01) |
| *G02B 6/02* | (2006.01) |
| *G02B 6/38* | (2006.01) |
| *G02B 6/26* | (2006.01) |
| *G02B 6/12* | (2006.01) |

(52) U.S. Cl.
CPC ..... *G01N 33/0036* (2013.01); *G02B 6/02328* (2013.01); *G02B 6/02361* (2013.01); *G02B 6/12* (2013.01); *G02B 6/26* (2013.01); *G02B 6/3833* (2013.01); *G02B 2006/12102* (2013.01)

(58) Field of Classification Search
CPC ............ G01N 33/0036; G02B 6/02328; G02B 6/02361; G02B 6/12; G02B 6/26; G02B 6/3833; G02B 2006/12102
USPC ........................................................ 73/31.05
See application file for complete search history.

(56) References Cited

U.S. PATENT DOCUMENTS

| | | | |
|---|---|---|---|
| 4,450,711 | A | 5/1984 | Claude |
| 5,301,538 | A | 4/1994 | Recla |
| 7,155,961 | B2 | 1/2007 | Fernandes |
| 8,418,529 | B2 | 4/2013 | Coudray et al. |
| 9,910,237 | B2 | 3/2018 | Spijker |
| 2010/0005860 | A1 | 1/2010 | Coudray et al. |
| 2014/0290343 | A1 | 10/2014 | Kulkarni et al. |
| 2015/0000382 | A1 | 1/2015 | Frucht |

(Continued)

FOREIGN PATENT DOCUMENTS

| | | | |
|---|---|---|---|
| WO | 2016005280 A1 | 1/2016 | |
| WO | 2017196449 A1 | 11/2017 | |
| WO | WO-2017196449 A1 * | 11/2017 | ......... G01N 21/3103 |

OTHER PUBLICATIONS

International Search Report and Written Opinion for International Application No. PCT/US2019/029914; International Filing Date Apr. 30, 2019; Report dated Aug. 14, 2019 (pp. 1-8).

(Continued)

*Primary Examiner* — Jerry M Blevins
(74) *Attorney, Agent, or Firm* — Cantor Colburn LLP

(57) ABSTRACT

A gas detector sensor node includes a first sensor conductor having a terminal end, a second sensor conductor including an end section, and a coupler joining the terminal end of the first sensor conductor with the end section of the second sensor conductor. The coupler is permeable to gas.

13 Claims, 4 Drawing Sheets

(56) References Cited

U.S. PATENT DOCUMENTS

| | | | |
|---|---|---|---|
| 2015/0160075 A1* | 6/2015 | Taverner | ................ G02B 6/125 |
| | | | 374/161 |
| 2017/0123147 A1* | 5/2017 | Brown | ..................... G02B 6/32 |
| 2017/0276894 A1 | 9/2017 | Green | |
| 2017/0343433 A1 | 11/2017 | Hill | |
| 2019/0071965 A1 | 3/2019 | Jaaskelainen et al. | |
| 2019/0339151 A1 | 11/2019 | Challener | |

OTHER PUBLICATIONS

International Search Report and Written Opinion for International Application No. PCT/US2019/029917; International Filing Date Apr. 30, 2019; Report dated Aug. 16, 2019 (pp. 1-8).

* cited by examiner

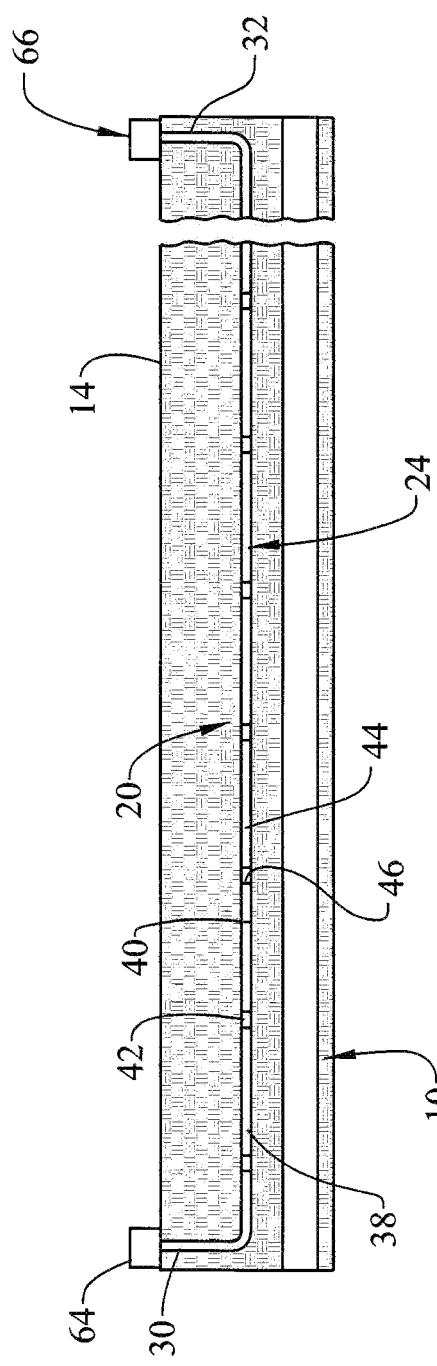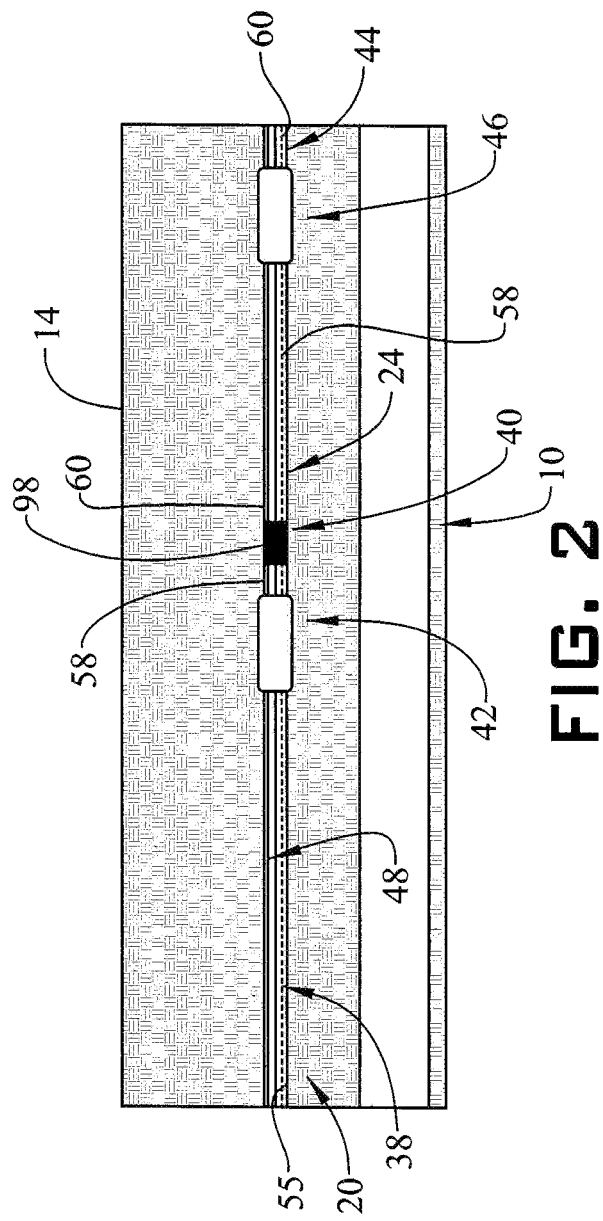

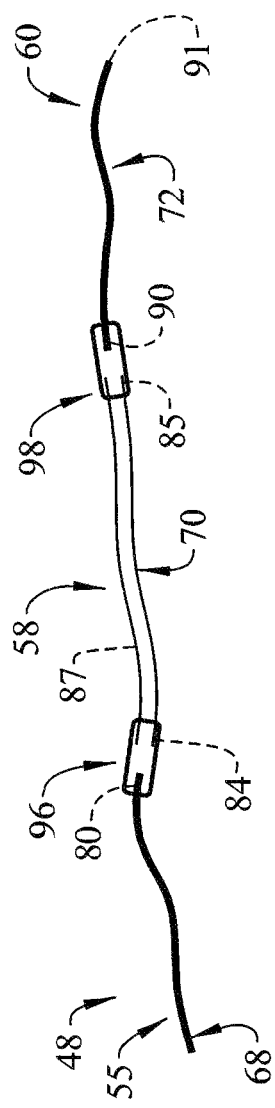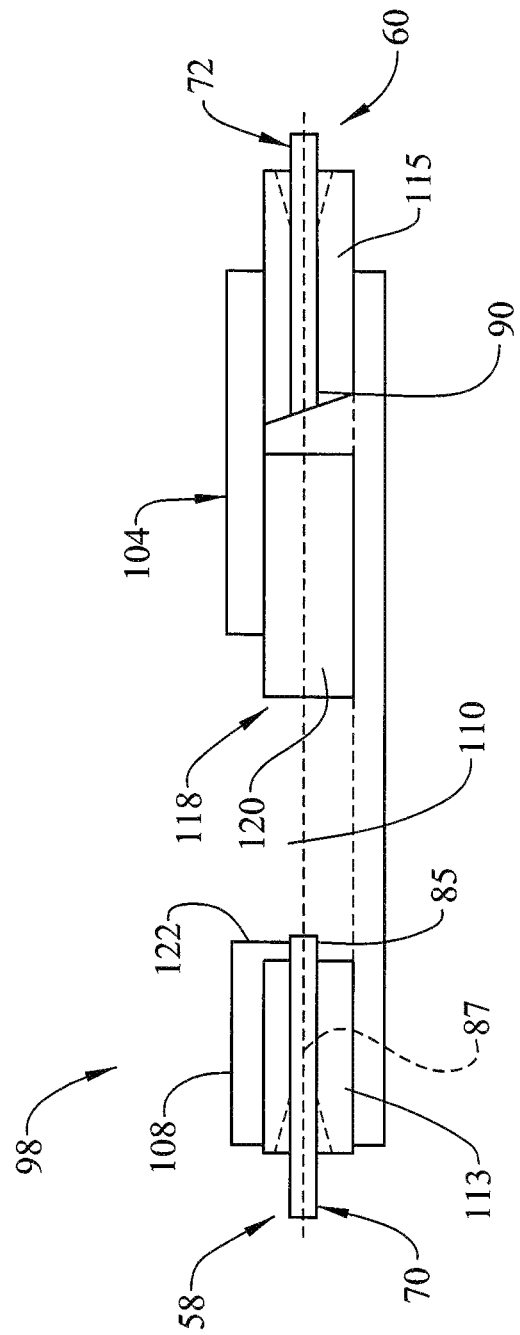

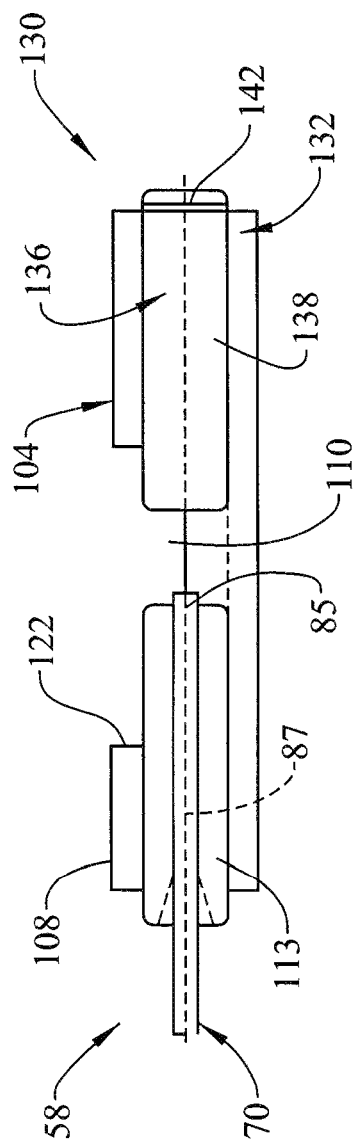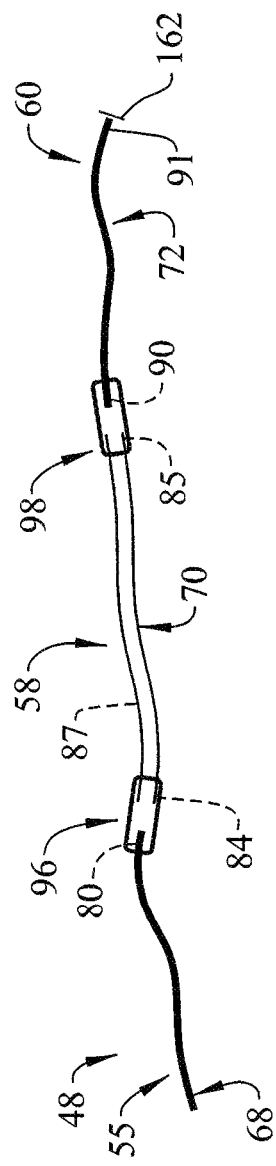

GAS SENSOR INCLUDING OPTIC FIBER CONNECTOR

CROSS REFERENCE TO RELATED APPLICATIONS

This application claims the benefit of an earlier filing date from U.S. Provisional Application Ser. No. 62/665,218, filed May 1, 2018, the entire disclosure of which is incorporated herein by reference.

STATEMENT OF GOVERNMENT SUPPORT

This invention was made with Government support under contract number DE-AR0000543 awarded by the Department of Energy. The Government has certain rights in this invention.

BACKGROUND

In subterranean fluid transport industry, various systems exist for detecting leaks. Further, various systems exist for transporting fluids including formation fluids. Pipelines may be employed, for example, to transport natural gas to and/or from a refinery. In many cases, the pipelines are subterranean. In order to detect leaks, a sensor line is buried with the pipeline.

A typical gas leak detector includes a sensing line having an inlet, an outlet, and a sensor arranged at the outlet. The sensing line is perforated, covered with a hydrophobic membrane and encased in a protective layer. The sensing line is given time to soak and absorb any gases that may be leaking from the pipeline. After a selected period, a purge flow is introduced into the inlet; and fluid passing from the outlet is monitored for a selected gas.

If gas is detected, steps may be taken to correct any leaks. A location of the leak may be correlated to an amount of time passed from fluid introduction and gas detection. Current sensing technology is typically limited to pipe lines that are no more than about 10 kilometers (km) due to the time required for the purge flow to clear the sensing line and due to the spreading of the leaking gas within the sensing tube during the purge which makes it more difficult to determine the leak location. That is, a typical sensing cycle for a 10 km sensing line is about 24 hours; 18 hours of soaking and 6 hours for the purge flow. Further, forming the sensor is a time-consuming process. Therefore, the art would appreciate a sensor system that might be used over greater distances and could be easier and more cost efficient to produce.

SUMMARY

Disclosed is a gas detector sensor node including a first sensor conductor having a terminal end, a second sensor conductor including an end section, and a coupler joining the terminal end of the first sensor conductor with the end section of the second sensor conductor. The coupler being permeable to gas.

BRIEF DESCRIPTION OF THE DRAWINGS

The following descriptions should not be considered limiting in any way. With reference to the accompanying drawings, like elements are numbered alike:

FIG. 1 depicts a subterranean gas line and gas sensor system including a gas sensing line and a plurality of sensor nodes, in accordance with an aspect of an exemplary embodiment;

FIG. 2 depicts a portion of the gas sensor system of FIG. 1, in accordance with an exemplary aspect;

FIG. 3 depicts a portion of a gas sensor system, in accordance with an aspect of an exemplary embodiment;

FIG. 4 depicts a coupler for a gas sensor system, in accordance with an aspect of an exemplary embodiment;

FIG. 5 depicts a coupler for a gas sensor system, in accordance with another aspect of an exemplary embodiment;

FIG. 6 depicts a portion of a gas sensor system, in accordance with another aspect of an exemplary embodiment.

DETAILED DESCRIPTION

Figure 7:
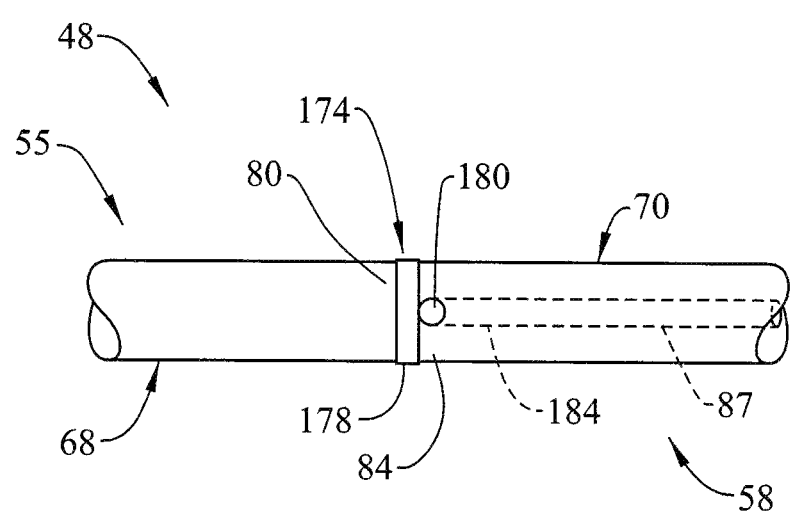
FIG. 7 depicts a coupler for a gas sensor system, in accordance with yet another aspect of an exemplary embodiment.

A detailed description of one or more embodiments of the disclosed apparatus and method are presented herein by way of exemplification and not limitation with reference to the Figures.

Referring to FIGS. 1 and 2, a gas pipeline is indicated generally at 10. Gas pipeline 10 may take the form of a subterranean pipeline buried beneath a surface 14. At this point, it should be understood that surface 14 may an exposed surface or surface 14 could represent a submersed surface. A gas sensor system 20 is buried adjacent to gas pipeline 10. In the embodiment shown, gas sensor system 20 is shown positioned above gas pipeline 10. However, it should be understood that the particular orientation of gas sensor system 20 relative to gas pipeline 10 may vary. It should also be understood that the gas sensor system described herein may be employed in connection with above-ground pipelines.

Gas sensor system 20 includes a sensing line 24 having a first end 30 and a second end 32. Sensing line 24 may be formed from a number of sections. For example, a first sensing line section 38 may be connected to a second sensing line section 40 by a sensor node 42. Second sensing line section 40 may be connected to a third sensing line section 44 through a second sensor node 46. The number of sensing line sections and sensor nodes may vary. Further a distance between adjacent sensor nodes may vary and could be up to 10 km or more. A sensing cable 48 (FIG. 2) extends along sensing line 24 and may pass through each sensor node. Sensing cable 48 may include a first sensor conductor 55 that extends to, for example, first sensor node 42 and a second sensor conductor 58 that extends between first sensor node 42 and second sensor node 46, and a third sensor conductor 60 extends from second sensor conductor.

Sensing line 24 and sensor cable 48 may be connected to a first control portion 64 arranged at, for example, first end 30 and a second control portion 66 arranged at, for example, second end 32. Sensing line 24 is allowed to "soak" or absorb any gas leaking from gas pipe line 10 for a period of time. After the period of time, the first control portion 64 may introduce a fluid, such as air, to purge sensing line 24. At the same time that the purge begins, control portion 64 may read a control signal passing through sensor cable 48 for signs of leaking gas that has diffused into sensing line 24 during the prior soak time. It should be understood that a purge flow, and sensor signal may be sent from and read at a single control portion.

Leaking gas may be pushed to a sensor node by the purge fluid. For example, sensing line 24 may be allowed to "soak" or absorb any gas that may be present adjacent to gas pipeline 10 for a first period of time and then be purged for a second period of time that is generally shorter than the first period of time. It is generally desirable that the second period of time be about one third of the first period of time so that any leaking gas that has diffused into the tube during the first period of time does not have enough time to diffuse back out of the tube during the purge or second period of time. During the second period of time, first and/or second control portions monitor the control signal passing through sensor cable 48 for signs of leaking gas at any one of the sensor nodes.

Referring to FIG. 3, first sensor conductor 55 may take the form of a solid core optic fiber 68, second sensor conductor 58 may take the form of a hollow core optic fiber 70 having a hollow interior section, and third sensor conductor 60 may take the form of a solid core optic fiber 72. First sensor conductor 55 is depicted as including a terminal end 80. Second sensor conductor 58 is shown with a first end section 84 and a second end section 85. A passage 87 extends between first end section 84 and second end section 85. Third sensor conductor 60 includes a first end portion 90 and a second end portion 91. At this point it should be understood that while described as being optic fibers, the sensor conductors may take on various forms.

In the exemplary embodiment depicted in FIG. 3, a first coupler 96 joins terminal end 80 of first sensor conductor 55 with first end section 84 of second sensor conductor 58. A second coupler 98 joins second end section 85 of second sensor conductor 58 with first end portion 90 of third sensor conductor 60. First coupler 96 may be arranged at first node 42 and second coupler 98 may be arranged downstream of first node 42 and upstream of second node 46. Each of first and second couplers 96 and 98 are permeable to gas so that gas may either enter conductor 70 or exit conductor 70 depending on the direction of gas flow. For example, first coupler 96 may receive gas that has been purged to first node 42 while second coupler 98 acts as an outlet for that gas.

Reference will now follow to FIG. 4 in describing second coupler 98 with an understanding that first coupler 96 may include similar structure. Second coupler 98 includes a body 104 that is permeable to gas. Body 104 may take the form of a sleeve 108 having a hollow interior 110. Second end section 85 of second sensor conductor 58 is secured to coupler 98 with a first connector 113 that extends into hollow interior 110. In this manner, passage 87 and hollow interior 110 may be fluidically connected. First end portion 90 of third sensor conductor 60 is secured to coupler 98 with a second connector 115.

In the exemplary aspect shown, a lens 118 is arranged in hollow interior 110 between second end section 85 of second sensor conductor 58 and first end portion 90 of third sensor conductor 60. Lens 118 may take the form of a gradient-index (GRIN) optics lens 120. However, it should be understood that lens 118 may take on other forms such as ball lenses, non-gradient refractive surfaces and the like. Light which may be transmitted from second end section 85 of the second sensor conductor 58 may diverge and thus may not be efficiently collected by third sensor conductor 60. Adding lens 118 increases light collection efficacy of third sensor conductor 60.

The particular position of lens 118 can be selected for more efficient transfer of the light between the second sensor conductor 58 and third sensor conductor 60. Depending on the focusing power of the lens, second and third sensor conductors 58 and 60 may be directly touching faces of lens 118. As an alternative, first and second sensor conductors 58 and 60 may be situated a short distance from lens 118. As an example, first and second sensor conductors 58 and 60 may be spaced about 1 to 3 mm from lens 118. Furthermore, although only a single lens is shown in FIG. 4, it is also possible to use multiple lenses to accomplish the same transfer of light from one conductor to the other conductor.

Changes in the light passing from second sensor conductor 58 to third sensor conductor 60 may indicate the presence of gas in, for example, first node 42. For example, gas which enters second sensor conductor 58 at first end section 84 may fill or partially fill passage 87 as it flows towards second end section 85. If the gas to be detected has an absorption line at a wavelength for which the conductors transmit light, then spectroscopy can be used to measure the absorption of light at that wavelength by any gas which is present in second sensor conductor 58. This may be readily accomplished by using, for example, a tunable laser to inject light into first sensor conductor 55 from first control portion 64 and allowing the light to interact with any gas present within second sensor conductor 58 before the laser light is returned by the third sensor conductor 60 to first control portion 64 or second control portion 66 for spectroscopic analysis. Further shown in FIG. 4, an opening 122 is formed in body 104. Opening 122 may take on a variety of forms. Opening 122 may serve as an outlet (not separately labeled) for gas flowing into coupler 98.

Reference will now be made to FIG. 5, wherein like reference numbers represent corresponding parts in the respective views in describing a coupler 130 in accordance with another exemplary aspect. In the embodiment shown, a second sensor conductor 132 take the form of a lens 136. Lens 136 may comprise a GRIN lens 138.

In this exemplary aspect, lens 136 includes a reflector 142. Light passing into lens 136 from first sensor conductor 58 may reflect back from reflector 142. The position of lens 136 may be selected to enhance efficacy of coupling reflected light back into first sensor conductor 58. In this manner, light passing back into first sensor conductor 58 may be evaluated for the presence of gas within. The use of the reflector may negate the need for a third conductor. The light from the one of first and second control portions 64 and 65 transmitted to lens 136 through first sensor conductor 58 is then conducted back to the one of the first and second control portions 64 and 65. In lieu of mounting a reflector to the lens, a reflector 162 may be connected to second end portion 91 of third sensor conductor 60 such as shown in FIG. 6, wherein like reference numerals represent corresponding parts in the respective views. Furthermore, reflector 162 may take the form of a Faraday reflector that reduces disturbances to the light such as birefringence caused by the conductors.

Reference will now follow to FIG. 7, wherein like reference numbers represent corresponding parts in the respective views in describing a coupler 174 in accordance with another aspect of an exemplary embodiment. Coupler 174 takes the form of a welded joint 178 having an opening 180 that is fluidically connected with a hollow interior 184 that may be defined by passage 87. Forming coupler 174 as a welded joint reduces size and manufacturing complexity by eliminating the need for a lens to couple light from one conductor to the next conductor. Instead, the opening 180 enables external gas to enter or exit second sensor conductor 58.

At this point, it should be understood that the exemplary embodiments describe a system for connecting sensing cable portions that promotes the detection of leaking gas. The couplers may take on a variety of forms and could include systems for passing light onward, or systems for reflecting light back to a source to be analyzed. Couplers may take the form of sleeves, welded joints and may or may not include reflective surfaces. Further, couplers may be provided with filtering systems that prevent dirt, dust and other debris from interfering with control signal inputs, or light signals passing to and/or from a node. It should also be understood that the couplers may be configured to transmit signals other than light through the sensing cable.

Set forth below are some embodiments of the foregoing disclosure:

Embodiment 1: A gas detector sensor node comprising: a first sensor conductor including a terminal end; a second sensor conductor including an end section; and a coupler joining the terminal end of the first sensor conductor with the end section of the second sensor conductor, the coupler being permeable to gas.

Embodiment 2: The gas detector sensor node as in any prior embodiment, wherein the coupler comprises a sleeve extending about the terminal end and the end section, the sleeve defining a hollow interior and including an opening.

Embodiment 3: The gas detector sensor node as in any prior embodiment, a reflector arranged at the sleeve at the end section of the second sensor conductor.

Embodiment 4: The gas detector sensor node as in any prior embodiment, wherein the second sensor conductor is defined by a lens.

Embodiment 5: The gas detector sensor node as in any prior embodiment, wherein the lens comprises a gradient-index (GRIN) optics lens.

Embodiment 6: The gas detector sensor node as in any prior embodiment, further comprising: a reflector arranged at the second sensor conductor spaced from the terminal end.

Embodiment 7: The gas detector sensor node as in any prior embodiment, wherein the second sensor conductor includes another end section spaced from the end section by a hollow interior section.

Embodiment 8: The gas detector sensor node as in any prior embodiment, further comprising: another coupler connected to the another end section, the coupler defining a gas inlet and the another coupler defining a gas outlet.

Embodiment 9: The gas detector sensor node as in any prior embodiment, further comprising: a reflector mounted to the another coupler.

Embodiment 10: The gas detector sensor node as in any prior embodiment, further comprising: a third sensor conductor including a first end portion connected to the another coupler and a second end portion.

Embodiment 11: The gas detector sensor node as in any prior embodiment, further comprising: a reflector arranged at the second end portion.

Embodiment 12: The gas detector sensor node as in any prior embodiment, wherein the coupler defines a welded joint.

Embodiment 13: The gas detector sensor node as in any prior embodiment, wherein the first sensor conductor is a solid core optic fiber.

Embodiment 14: The gas detector sensor node as in any prior embodiment, wherein the second sensor conductor comprises a hollow core optic fiber including a hollow interior portion.

Embodiment 15: The gas detector sensor node as in any prior embodiment, wherein the welded joint includes an opening fluidically connected with the hollow interior portion.

The use of the terms "a" and "an" and "the" and similar referents in the context of describing the invention (especially in the context of the following claims) are to be construed to cover both the singular and the plural, unless otherwise indicated herein or clearly contradicted by context. Further, it should be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited.

What is claimed is:

1. A gas detector sensor node comprising:
    a first sensor conductor including a terminal end, the first sensor conductor being a solid core conductor;
    a second sensor conductor including a first end section and a second end section, the second sensor conductor being a hollow core conductor;
    a third sensor conductor including a first end portion, the third sensor conductor being a solid core conductor;
    a first coupler joining the terminal end of the first sensor conductor with the first end section of the second sensor conductor, the first coupler being permeable to gas; and
    a second coupler joining the second end section of the second sensor conductor with the first end portion of the third sensor conductor, the second sensor conductor being permeable to gas.

2. The gas detector sensor node according to claim 1, wherein the first coupler comprises a sleeve extending about the terminal end and the end section, the sleeve defining a hollow interior and including an opening.

3. The gas detector sensor node according to claim 2, a reflector arranged at the sleeve at the end section of the second sensor conductor.

4. The gas detector sensor node according to claim 2, wherein the second sensor conductor is defined by a lens.

5. The gas detector sensor node according to claim 4, wherein the lens comprises a gradient-index (GRIN) optics lens.

6. The gas detector sensor node according to claim 4, further comprising: a reflector arranged at the second sensor conductor spaced from the terminal end.

7. The gas detector sensor node according to claim 1, further comprising: a reflector mounted to the second coupler.

8. The gas detector sensor node according to claim 1, further comprising: a wherein the third sensor conductor includes a second end portion.

9. The gas detector sensor node according to claim 8, further comprising: a reflector arranged at the second end portion.

10. The gas detector sensor node according to claim 1, wherein the first coupler defines a welded joint.

11. The gas detector sensor node according to claim 10, wherein the first sensor conductor is a solid core optic fiber.

12. The gas detector sensor node according to claim 11, wherein the second sensor conductor comprises a hollow core optic fiber including a hollow interior portion.

13. The gas detector sensor node according to claim 12, wherein the welded joint includes an opening fluidically connected with the hollow interior portion.

\* \* \* \* \*